US012636181B2

(12) United States Patent
Frantz et al.

(10) Patent No.: US 12,636,181 B2
(45) Date of Patent: **\*May 26, 2026**

(54) ADJUSTABLE THERMOPLASTIC DENTAL APPLIANCE SYSTEM AND METHOD

(71) Applicant: Frantz Design Incorporated, Katy, TX (US)

(72) Inventors: Joseph Lee Frantz, Spicewood, TX (US); Donald E. Frantz, Pasadena, TX (US)

(73) Assignee: FRANTZ DESIGN INCORPORATED, Katy, TX (US)

( \* ) Notice: Subject to any disclaimer, the term of this patent is extended or adjusted under 35 U.S.C. 154(b) by 241 days.

This patent is subject to a terminal disclaimer.

(21) Appl. No.: 18/144,035

(22) Filed: May 5, 2023

(65) Prior Publication Data

US 2023/0270587 A1 Aug. 31, 2023

Related U.S. Application Data

(63) Continuation-in-part of application No. 17/892,118, filed on Aug. 21, 2022, now Pat. No. 11,793,668, (Continued)

(51) Int. Cl.
*A61F 5/56* (2006.01)
*B29C 45/14* (2006.01)
(Continued)

(52) U.S. Cl.
CPC .......... *A61F 5/566* (2013.01); *B29C 45/1671* (2013.01); *B33Y 80/00* (2014.12);
(Continued)

(58) Field of Classification Search
CPC .... A61F 5/566; A61F 5/58; A61F 5/56; A61F 2005/563; A61C 7/08; A61C 19/063;
(Continued)

(56) References Cited

U.S. PATENT DOCUMENTS

| | | | |
|---|---|---|---|
| 6,109,265 A | 8/2000 | Franz et al. | |
| 7,637,262 B2 | 12/2009 | Bailey | |

(Continued)

*Primary Examiner* — Tarla R Patel
(74) *Attorney, Agent, or Firm* — Glenn Gold, P.A.; Glenn E. Gold

(57) ABSTRACT

Methods and systems herein relate to forming an upper dental appliance chassis including at least two upper appliance button protrusions; forming a lower dental appliance chassis including at least two lower appliance button protrusions and at least two vertical displacement bite pads; injection overmolding a first thermoplastic on the upper dental appliance chassis to provide a first reformable thermoplastic layer integrated with the upper dental appliance chassis that exposes the at least two upper appliance button protrusions to form an upper dental tray; and injection overmolding a second thermoplastic on the upper dental appliance chassis to provide a second reformable thermoplastic layer integrated with the lower dental appliance chassis that exposes the at least two lower appliance button protrusions and the at least two vertical displacement bite pads to form a bottom dental tray.

15 Claims, 8 Drawing Sheets

Related U.S. Application Data which is a continuation of application No. 16/773,255, filed on Jan. 27, 2020, now Pat. No. 11,419,751, which is a continuation-in-part of application No. 16/631,160, filed on Jan. 14, 2020, now Pat. No. 11,185,436, and a continuation-in-part of application No. 16/248,602, filed on Jan. 15, 2019, now Pat. No. 11,357,661, and a continuation-in-part of application No. 16/189,140, filed on Nov. 13, 2018, now Pat. No. 11,109,998.

(60) Provisional application No. 62/797,889, filed on Jan. 28, 2019.

(51) Int. Cl.

| | |
|---|---|
| *B29C 45/16* | (2006.01) |
| *B29C 51/10* | (2006.01) |
| *B29C 51/46* | (2006.01) |
| *B29C 64/00* | (2017.01) |
| *B29C 64/112* | (2017.01) |
| *B29C 64/118* | (2017.01) |
| *B29C 64/386* | (2017.01) |
| *B29C 65/08* | (2006.01) |
| *B29C 69/00* | (2006.01) |
| *B29K 23/00* | (2006.01) |
| *B29K 67/00* | (2006.01) |
| *B29K 71/00* | (2006.01) |
| *B29K 75/00* | (2006.01) |
| *B29K 105/00* | (2006.01) |
| *B29L 31/00* | (2006.01) |
| *B33Y 10/00* | (2015.01) |
| *B33Y 30/00* | (2015.01) |
| *B33Y 50/02* | (2015.01) |
| *B33Y 80/00* | (2015.01) |
| *G16H 40/67* | (2018.01) |

(52) U.S. Cl.
CPC .. *B29C 45/14336* (2013.01); *B29C 45/14778* (2013.01); *B29K 2023/16* (2013.01); *B29K 2067/00* (2013.01); *B29K 2067/003* (2013.01); *B29K 2071/02* (2013.01); *B29K 2075/00* (2013.01); *B29L 2031/753* (2013.01); *B33Y 10/00* (2014.12)

(58) Field of Classification Search
CPC ... A61B 5/4547; A61B 5/4552; A61B 5/4557; A61B 5/682; A61B 5/0534; A63B 71/085; A63B 2071/086; A63B 2017/088; B29C 64/00; B29C 64/386; B29C 69/001; B29C 64/118; B29C 64/112; B29C 51/10; B29C 51/46; B33Y 10/00; B33Y 30/00; B33Y 50/02; B29K 2105/256; B29L 2031/753
See application file for complete search history.

(56) References Cited

U.S. PATENT DOCUMENTS

| | | | |
|---|---|---|---|
| 10,596,027 B2 | 3/2020 | Thornton et al. | |
| 11,185,436 B2 * | 11/2021 | Frantz | A61F 5/566 |
| 11,419,751 B2 * | 8/2022 | Frantz | B33Y 80/00 |
| 11,793,668 B2 * | 10/2023 | Frantz | B29C 45/1671 |
| 2009/0014013 A1 | 1/2009 | Magnin | |
| 2009/0032030 A1 | 2/2009 | Callender | |
| 2009/0036889 A1 | 2/2009 | Callender | |

* cited by examiner

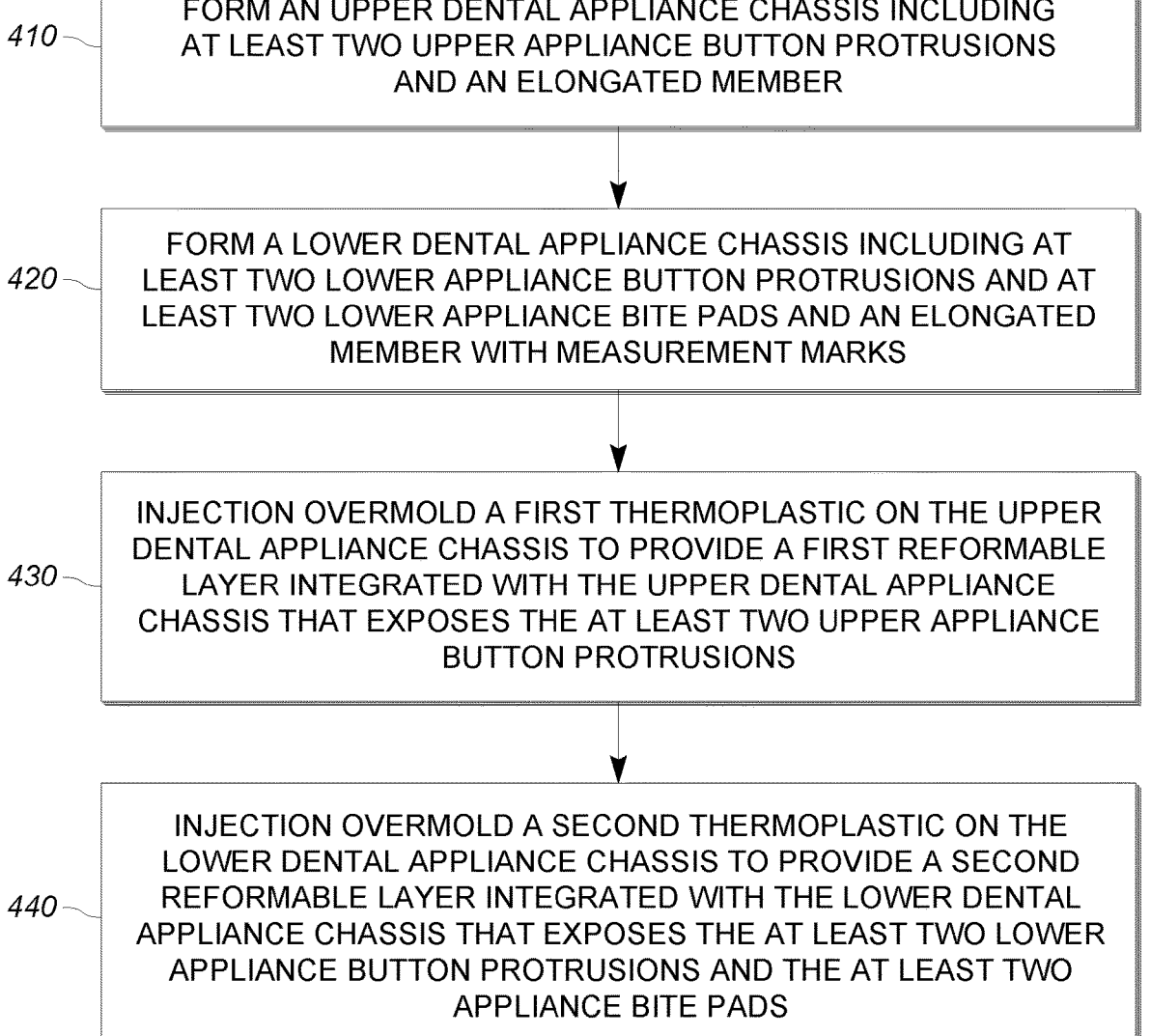

410 — FORM AN UPPER DENTAL APPLIANCE CHASSIS INCLUDING AT LEAST TWO UPPER APPLIANCE BUTTON PROTRUSIONS AND AN ELONGATED MEMBER

420 — FORM A LOWER DENTAL APPLIANCE CHASSIS INCLUDING AT LEAST TWO LOWER APPLIANCE BUTTON PROTRUSIONS AND AT LEAST TWO LOWER APPLIANCE BITE PADS AND AN ELONGATED MEMBER WITH MEASUREMENT MARKS

430 — INJECTION OVERMOLD A FIRST THERMOPLASTIC ON THE UPPER DENTAL APPLIANCE CHASSIS TO PROVIDE A FIRST REFORMABLE LAYER INTEGRATED WITH THE UPPER DENTAL APPLIANCE CHASSIS THAT EXPOSES THE AT LEAST TWO UPPER APPLIANCE BUTTON PROTRUSIONS

440 — INJECTION OVERMOLD A SECOND THERMOPLASTIC ON THE LOWER DENTAL APPLIANCE CHASSIS TO PROVIDE A SECOND REFORMABLE LAYER INTEGRATED WITH THE LOWER DENTAL APPLIANCE CHASSIS THAT EXPOSES THE AT LEAST TWO LOWER APPLIANCE BUTTON PROTRUSIONS AND THE AT LEAST TWO APPLIANCE BITE PADS

FIG. 4

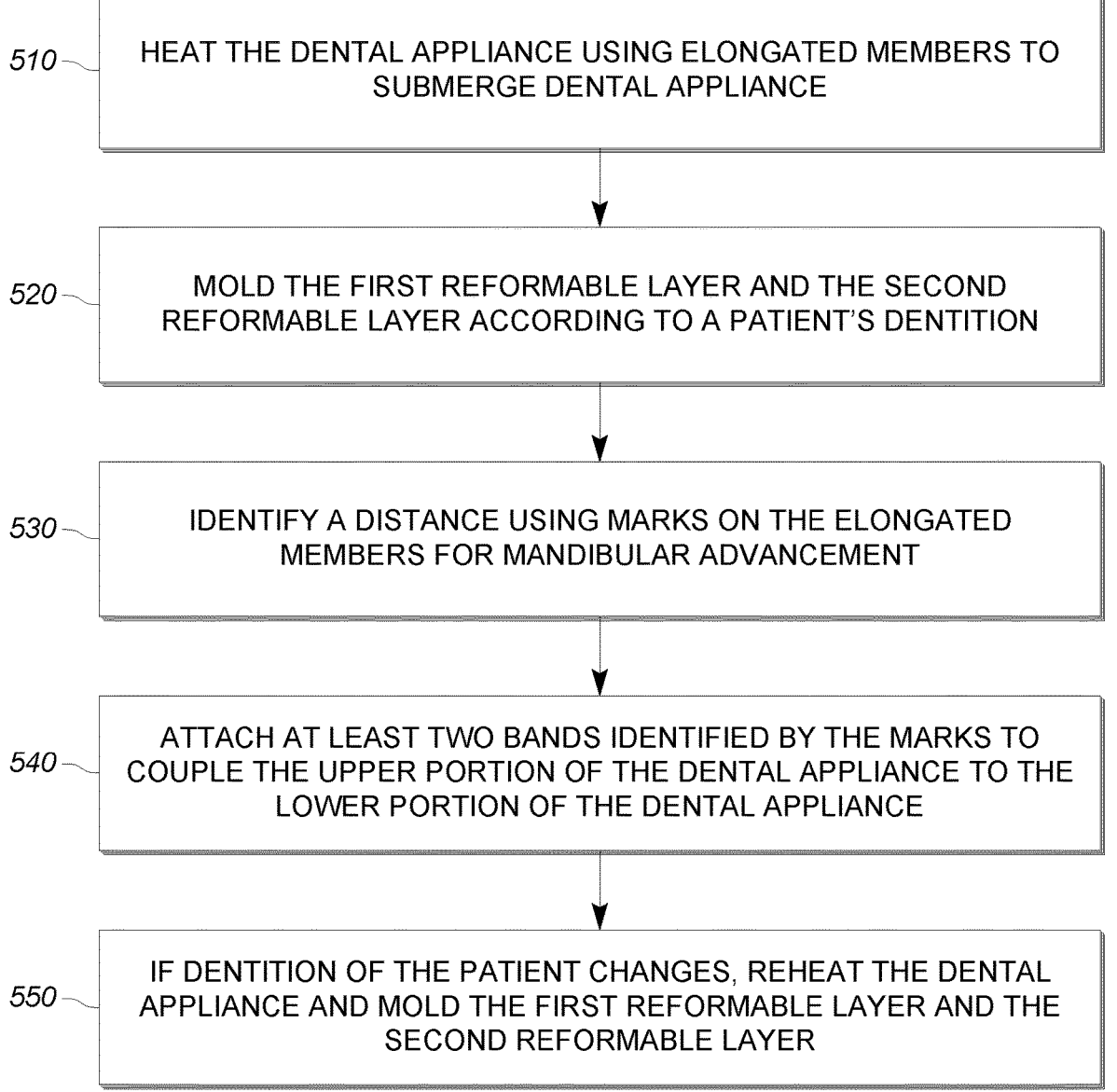

510 — HEAT THE DENTAL APPLIANCE USING ELONGATED MEMBERS TO SUBMERGE DENTAL APPLIANCE

520 — MOLD THE FIRST REFORMABLE LAYER AND THE SECOND REFORMABLE LAYER ACCORDING TO A PATIENT'S DENTITION

530 — IDENTIFY A DISTANCE USING MARKS ON THE ELONGATED MEMBERS FOR MANDIBULAR ADVANCEMENT

540 — ATTACH AT LEAST TWO BANDS IDENTIFIED BY THE MARKS TO COUPLE THE UPPER PORTION OF THE DENTAL APPLIANCE TO THE LOWER PORTION OF THE DENTAL APPLIANCE

550 — IF DENTITION OF THE PATIENT CHANGES, REHEAT THE DENTAL APPLIANCE AND MOLD THE FIRST REFORMABLE LAYER AND THE SECOND REFORMABLE LAYER

ADJUSTABLE THERMOPLASTIC DENTAL APPLIANCE SYSTEM AND METHOD

CROSS-REFERENCE TO RELATED APPLICATIONS

The present application is a continuation-in-part of pending U.S. patent application Ser. No. 17/892,118 entitled "Thermoplastic Dental Appliance System and Method," filed Aug. 21, 2022, which is hereby incorporated by reference in its entirety, which is a continuation of U.S. Pat. No. 11,419,751, which was a non-provisional filing of U.S. Provisional Patent Application Ser. No. 62/797,889, entitled "Thermoplastic Dental Appliance System and Method," filed Jan. 28, 2019, which is hereby incorporated by reference in its entirety.

BACKGROUND

Sleep apnea and obstructive sleep apnea treatments include surgery, positive airflow machinery, such as CPAP machines, and dental appliances. One known dental appliance is the "Elastic Mandiblular Advancement" (EMA®) and related appliances. The EMA® appliance operates by providing increased airflow by forward mandibular advancement. One problem with the EMA® appliance is that each appliance requires the specific dentition of a patient to create the appliance. What is needed is a solution that avoids the need for the specific dentition of a patient prior to formation of an appliance.

SUMMARY

Some embodiments of a method may include forming an upper dental appliance chassis including at least two upper appliance button protrusions and an elongated member protruding from the upper dental appliance chassis, forming a lower dental appliance chassis including at least two lower appliance button protrusions, at least two vertical displacement bite pads, and a second elongated member protruding from the lower dental appliance chassis, injection overmolding a first thermoplastic on the upper dental appliance chassis to provide a first reformable layer integrated with the upper dental appliance chassis that exposes the at least two upper appliance button protrusions to form an upper dental tray, and injection overmolding a second thermoplastic on the lower dental appliance chassis to provide a second reformable layer integrated with the lower dental appliance chassis that exposes the at least two lower appliance button protrusions and the at least two vertical displacement bite pads to form a bottom dental tray, wherein the at least two vertical displacement bite pads include a gradient inclining from rear to fore.

The method further includes forming a dental appliance including the upper dental appliance chassis and the lower dental appliance chassis, wherein the at least two lower appliance button protrusions, and the at least two upper appliance button protrusions provide a forward mandibular position when two or more bands are attached to connect the upper dental tray and the lower dental tray.

In one or more embodiments, the upper dental appliance chassis and the lower dental appliance chassis are injection molded from one or more of an Ethylene Propylene Copolymer and a Polyoxymethlene Copolymer.

In one or more embodiments, the upper dental appliance chassis and the lower dental appliance chassis are injection molded using a thermoplastic olefin, thermoplastic polyolefin, or olefinic thermoplastic elastomer.

In one or more embodiments, the upper dental appliance chassis and the lower dental appliance chassis are injection molded using a polyethylene terephthalate.

In one or more embodiments, the upper dental appliance chassis and the lower dental appliance chassis are formed by three-dimensional (3D) printing of one or more of a light polymerizable liquid thermoset crosslinked polymer, a polyurethane, a methacrylate and a copolymer.

In one or more embodiments, the upper dental appliance chassis and the lower dental appliance chassis are formed by three-dimensional (3D) printing of a polymerizable resin composition of a urethane monomer of urethane dimethacrylate (UDMA), an acidic monomer, and one or more hydrophobic monomers.

In one or more embodiments, the first thermoplastic and the second thermoplastic are comprised of one or more of an ε-caprolactone, caprolactam and one or more polycaprolactone polymers.

In one or more embodiments, the first thermoplastic and the second thermoplastic are comprised of one or more of a caprolactone or polycaprolactone polymer material overmolded on the upper dental appliance chassis and the lower dental appliance chassis.

In one or more embodiments, the at least two vertical displacement bite pads are configured to be replaced with alternate vertical displacement bite pads of one or more heights.

Another embodiment is directed to a mandibular advancement dental appliance including a two-layer upper tray including an upper dental appliance chassis layer including at least two upper appliance button protrusions and a first elongated member protruding from the upper dental appliance chassis; and a first reformable thermoplastic layer injection overmolded over a portion of the upper dental appliance chassis layer formed of one or more of an ε-caprolactone, caprolactam and one or more polycaprolactone polymers integrated with the upper dental appliance chassis via one or more cavities in the surface of the upper dental appliance chassis, the first reformable thermoplastic layer configured to expose the at least two upper appliance button protrusions; a two-layer lower tray including a lower dental appliance chassis layer including at least two lower appliance button protrusions and at least two vertical displacement bite pads, and a second elongated member protruding from the lower dental appliance chassis; and a second reformable thermoplastic layer injection overmolded over the lower dental appliance chassis layer formed of one or more of an ε-caprolactone, caprolactam and one or more polycaprolactone polymers integrated with the lower dental appliance chassis via one or more cavities in the surface of the lower dental appliance chassis, the second reformable thermoplastic layer configured to expose the at least two lower appliance button protrusions and the at least two vertical displacement bite pads, wherein the at least two vertical displacement bite pads include a gradient inclining from rear to fore.

In one or more embodiments, the mandibular advancement dental appliance includes a pair of bands adapted to couple the two-layer lower tray with the two-layer upper tray to provide mandibular advancement. In other embodiments, the first elongated member and the second elongated member include marks to measure forward mandibular adjustment when worn by a patient. Further, in one or more embodiments, the first elongated member and/or the second elongated member include a default 21 millimeter marking and at least one of the first elongated member and the second elongated member include marks that identify a displacement matching a length for the pair of bands.

In one or more embodiments, the mandibular advancement dental appliance of claim includes a pair of bands adapted to couple the two-layer lower tray with the two-layer upper tray to provide mandibular advancement.

Some embodiments include a processor and a non-transitory computer-readable storage medium storing instructions operative when executed on the processor to perform the methods herein described.

BRIEF DESCRIPTION OF THE DRAWINGS

FIG. 4 illustrates a method in accordance with one or more embodiments of the present disclosure.

FIG. 5 illustrates another method in accordance with one or more embodiments of the present disclosure.

DETAILED DESCRIPTION

Figure 1:
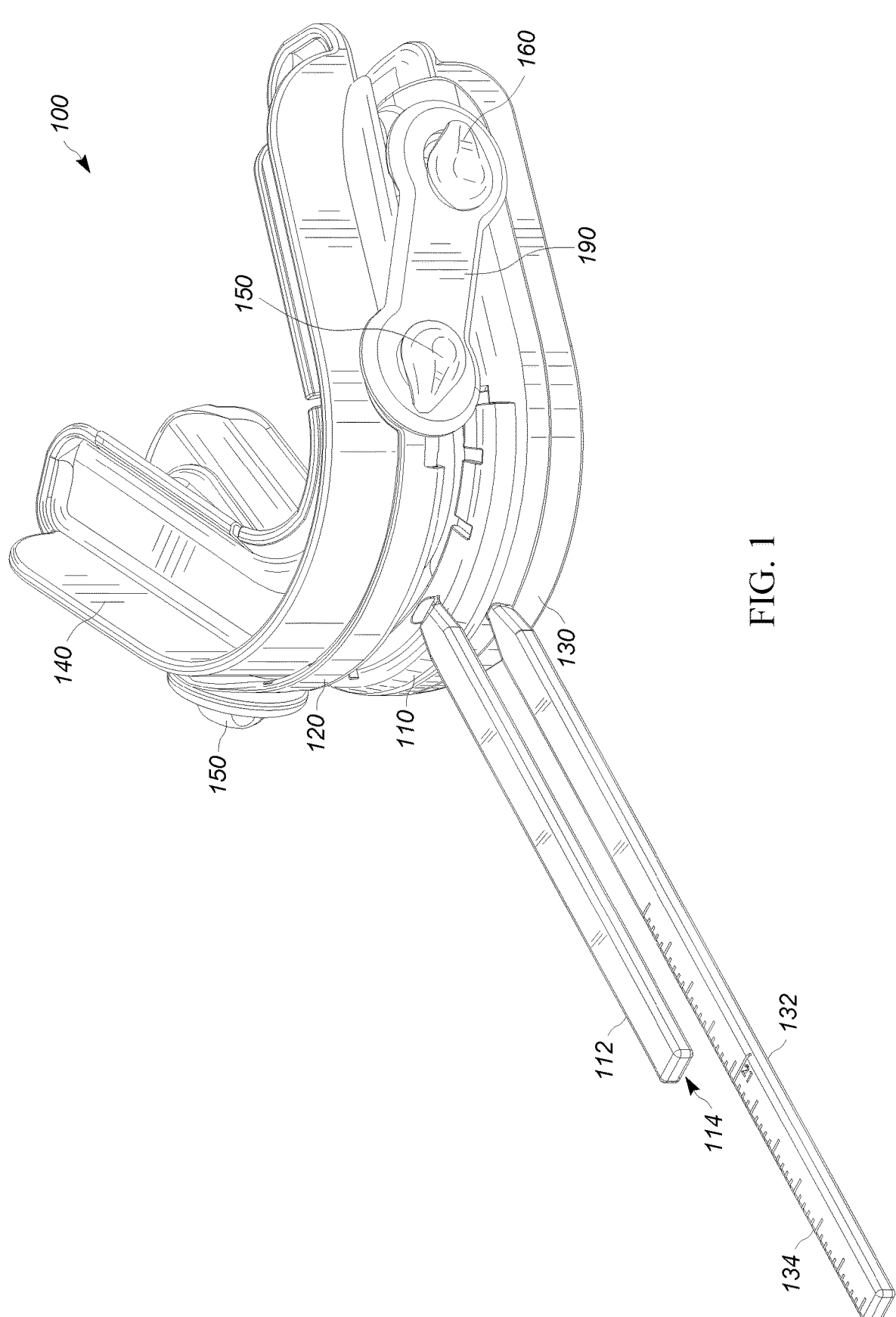
FIG. 1 illustrates a thermoplastic dental appliance including straps, button protrusions and a vertical displacement bite pads by overmolding manufacture in accordance with one or more embodiments of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Referring now to FIG. 1, a dental appliance in accordance with one or more embodiments is illustrated. Unlike other dental appliances, the illustrated dental appliance provides a "boil and bite" type of appliance that produces an elasto-mandibular advancement appropriate for treating snoring and sleep apnea. The dental appliance 100 is formed by having lower dental chassis 110 and upper dental chassis 120 overmolded with a reformable thermoplastic layers 130 and 140. Lower dental chassis 110 and upper dental chassis 120 can be injection molded or 3D printed of a non-reformable material. The reformable thermoplastic overmolded material in layers 130 and 140 couples to the layer of non-reformable material by virtue of a plurality of cavities within upper and lower chassis 110, 120.

In one or more embodiments, the lower dental chassis 110 and the upper dental chassis 120 include button protrusions, two on each of dental chassis 110, 120. Button protrusions shown in FIG. 1 include upper button protrusions 150 and lower button protrusion 160. FIG. 1 further includes elongated members 112 and 132, with elongated member 112 attached to upper dental chassis 120, and elongated member 132 attached to lower dental chassis 110. In one or more embodiments, elongated members 112 and 132 include measurements, such as marks to enable proper titration and choice of band 190 for a patient.

More particularly, as shown in FIG. 1, lower dental chassis 110 includes elongated member 132 with measurement markings 134 which may be millimeter markings that function to identify a length of band that is appropriate for preventing sleep apnea and snoring of a patient. In an embodiment, when the upper dental chassis 120 and the lower dental chassis 110 are aligned one on top of the other, the end of elongated member 112, shown as end 114, aligns with measurement marking 132. In one embodiment, this mark may be a "21" to indicate that a 21 millimeter length band is appropriate for a patient to achieve forward mandibular advancement that aligns the teeth enough to prevent sleep apnea.

Since not all patients have mandibles that achieve proper advancement with a 21 millimeter length band or strap, markings on the elongated members enable fitting of the dental appliance to determine a proper length of band. For example, if a patient inserts the dental appliance after form fitting the appliance to their dentition, the patient may then determine a proper alignment and horizontal advancement that is comfortable and achieves a forward mandibular advancement appropriate for the patients mouth. Next, the markings on the elongated members assist to determine the size band that is associated with that alignment. For example, where the end of the top elongated member 112 sits relative to the bottom elongated member 132 indicates the type of band required. Thus, if a patient needs greater advancement than where the upper elongated member 112 mark 114 aligns with "21" then the displacement is shown on measurement marks 132 in terms of millimeters. A one millimeter displacement of further mandibular advancement would indicate that a 20 millimeter band be appropriate for the given patient. Conversely, if a patient has an overbite, a longer band would be more appropriate as indicated by the amount by which the upper elongated member 112 mark 114 sits relative to the mark "21" and would indicate how many millimeters beyond a 21 millimeter band would be appropriate for comfortable advancement.

Figure 2:
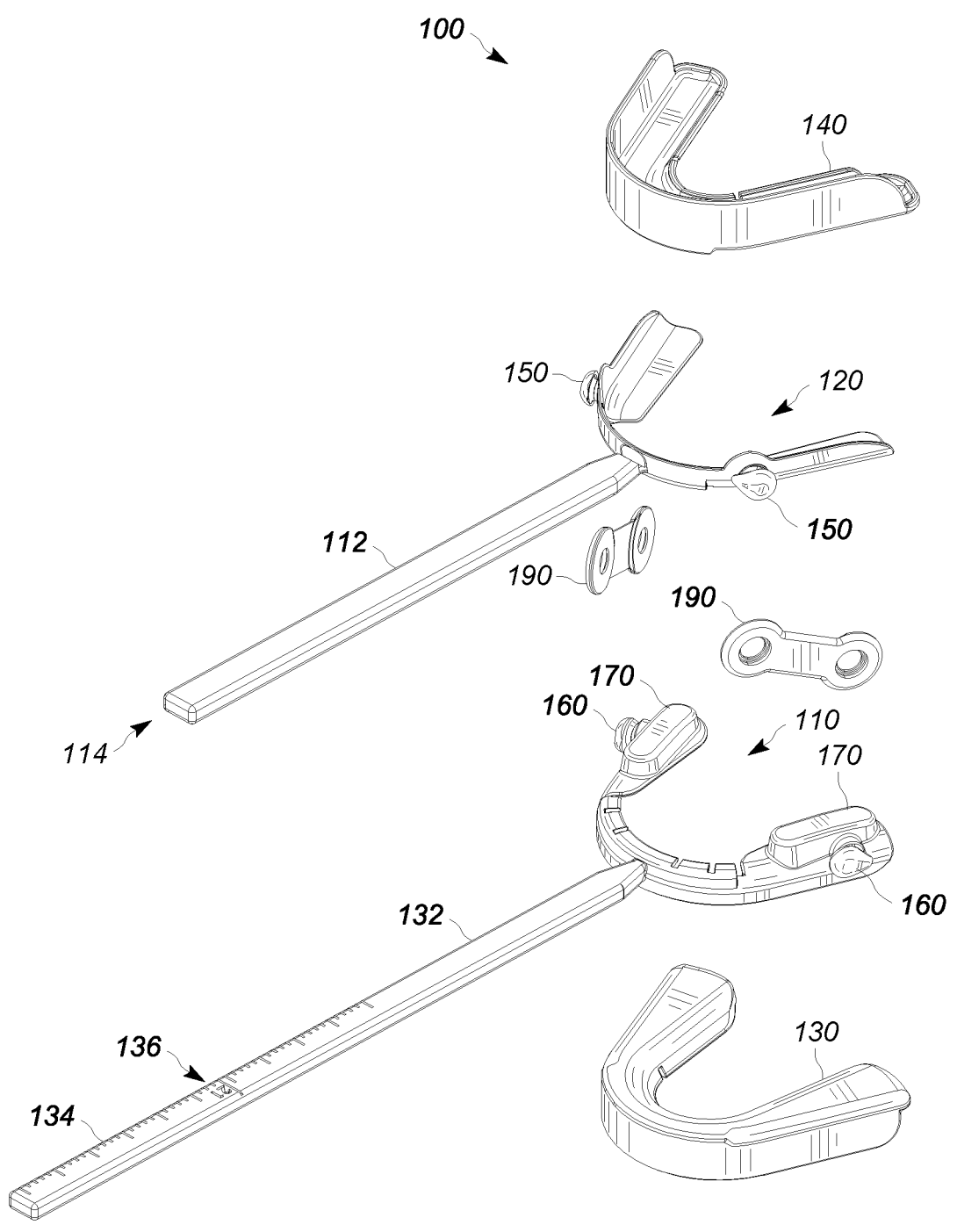
FIG. 2 illustrates a top exploded view of a thermoplastic dental appliance including straps, button protrusions and bit pads illustrating the overmolded dentition layer in accordance with one or more embodiments of the present disclosure.
Figure 3:
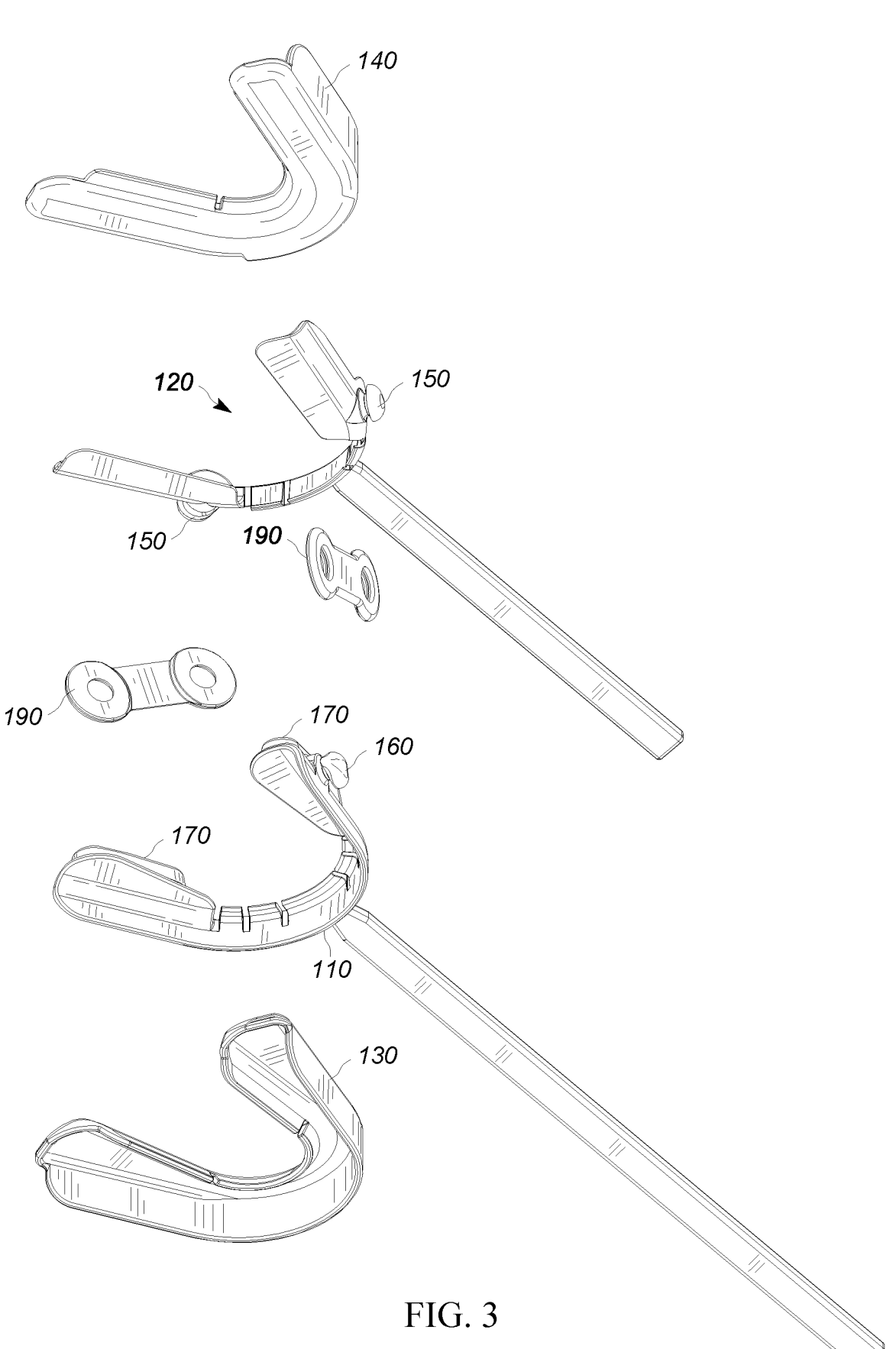
FIG. 3 illustrates a bottom exploded view of a thermoplastic dental appliance including straps, button protrusions and bit pads illustrating the overmolded dentition layer in accordance with one or more embodiments of the present disclosure.

Referring now to FIGS. 2 and 3, exploded views of the dental appliance illustrate how different components fit together to create a dental appliance appropriate for treating sleep apnea.

As shown, FIGS. 2 and 3 show lower dental chassis 110, and upper dental chassis 120 and illustrate cavities to enable secure coupling to reformable thermoplastic layers 130 and 140 via injection overmolding. Bottom lower dental chassis 110 further includes button protrusions 160, bite pads 170, and elongated member 130 with measurement markings 132 and marking "21" 136. In one embodiment, bite pads 170 includes alternate snap-on type bite pads to enable different heights of vertical displacement as appropriate for a patient. In another embodiment bite pads 170 include an increasing gradient from rear to fore to provide more comfort for a patient. More particularly, in one embodiment, either the injection molded bite pads or snap-on type bite pads include a one to two millimeter gradient from rear to fore to enable movement FIGS. 2 and 3 further show elastic bands 190 configured to couple the lower dental chassis 110 to upper dental chassis 120. As shown, upper dental chassis 120 includes button protrusions 150 for receiving elastic bands 190. FIGS. 2 and 3 further illustrate that upper dental chassis 120 includes cavities for receiving reformable thermoplastic layer 140 through injection overmolding.

Referring now to FIG. 4, a flow diagram illustrates a method for forming a dental appliance. As shown, block 410 provides for forming an upper dental appliance chassis including at least two upper appliance button protrusions 150 and an elongated member 112. For example, lower dental chassis 110 and upper dental chassis 120 are formed via one or more of injection molding and 3D printing.

Block 420 provides for forming a lower dental appliance chassis 110 including at least two lower appliance button protrusions 160, at least two lower appliance bite pads 170, and an elongated member 132 with measurement marks 134 and 136. For example, both lower dental appliance chassis 110 and upper dental appliance chassis 120 can be formed by injection molding or 3D printing a nonreformable thermoplastic, nylon or other nonreformable material.

Block 430 provides for injection overmolding a first thermoplastic on the upper dental appliance chassis to provide a first reformable layer integrated with the upper dental appliance chassis that exposes the at least two upper appliance button protrusions. For example, both lower dental appliance chassis 110 and upper dental appliance chassis 120 can be formed by injection molding or 3D printing a nonreformable thermoplastic, nylon or other nonreformable material. In one or more embodiments, the upper dental appliance chassis and the lower dental appliance chassis are injection molded from one or more of an Ethylene Propylene Copolymer and a Polyoxymethlene Copolymer. In one or more embodiments, the upper dental appliance chassis and the lower dental appliance chassis can be injection molded using a thermoplastic olefin, thermoplastic polyolefin, or an olefinic thermoplastic elastomer. In one or more embodiments, the upper dental appliance chassis and the lower dental appliance chassis are injection molded using a polyethylene terephthalate.

In other embodiments, the upper dental appliance chassis and the lower dental appliance chassis are formed by three-dimensional (3D) printing of one or more of a light polymerizable liquid thermoset crosslinked polymer, a polyurethane, a methacrylate and a copolymer. In one or more embodiments, the upper dental appliance chassis and the lower dental appliance chassis can be formed by three-dimensional (3D) printing of a polymerizable resin composition of a urethane monomer of urethane dimethacrylate (UDMA), an acidic monomer, and one or more hydrophobic monomers.

Referring back to FIG. 4, block 440 provides for injection overmolding a second thermoplastic on the lower dental appliance chassis to provide a second reformable layer integrated with the lower dental appliance chassis that exposes the at least two lower appliance button protrusions and the at least two appliance bit pads. For example, referring to FIGS. 2 and 3, injection overmolding a reformable thermoplastic 130 over lower dental appliance chassis 110 enables integration of the lower dental appliance chassis 110 with reformable thermoplastic 130. In one or more embodiments, lower dental appliance chassis 110 includes cavities or deformations that provide a surface for better adhesion of the reformable thermoplastic 130 to the lower dental appliance chassis 110.

The materials appropriate for a three-dimensional printer can be resin-type materials and materials described in U.S. Pat. No. 9,682,018 to Sadowsky et al., Jun. 20, 2017, "Denture Tooth and Material" which is hereby incorporated by reference in its entirety. As one of skill in the art will appreciate, materials appropriate for dental appliances must be FDA approved. Appropriate materials for resins is further described in Tanaka J, Hashimoto T., Stansbury J W, Antonucci J M, Suzuki K., "Polymer Properties of Resins Composed of UDMA an Methacrylates With the Carboxyl Group" Dental Material Journal 2001; 10:206-215, which incorporated by reference herein in its entirety.

Three-dimensional printing, as referred to herein include, but is not limited to, stereolithography (SLA), micro-stereolithography (pSLA), DLP projection, 2PP (two photon polymerization), continuous liquid interface production and material jetting. In embodiments, three-dimensional printing includes a layer-by-layer printing with successive layers formed in discrete layers. For example, a surface with a build plate immersed in a reservoir of a formulation of a polymer/resin component can be exposed to light at wavelengths and intensity to activate a photoinitiator to cause photopolymerization. As one of skill in the art will appreciate, there are other methods of three-dimensional printing such as continuous liquid interphase printing, in which dental trays are built up from a reservoir of photopolymerizable resin. Continuous liquid interphase printing is described in U.S. Patent Publication Nos. 2015/0097315, 2015/0097316, and 2015/0102532, the disclosures of each of which are incorporated herein by reference in their entirety.

Thus, as shown above, the upper and lower dental appliance chassis portion of a dental appliance can be directly manufactured using 3D technology. Material appropriate for 3D printing technology include thermoset polymers such as light polymerizable liquid materials. In one or more embodiments, the material appropriate for 3D printing includes a crosslinked polymer, such as a polyurethane, a methacrylate or a copolymer. In some embodiments, 3D printing materials can include nylon materials.

In one or more embodiments, the materials used for milling and/or injection molding of can be provided by Myerson Tooth, Inc., including VisiClear™, and Dura-Flex™, which are Ethylene Propylene Copolymers having the following properties as shown in Table 1:

TABLE 1

|  | Test Method | Nominal Value Unit |
|---|---|---|
| Physical |  |  |
| Density-Specific Gravity (Method B) | ASTM D792 | .902 sp gr 23/23° C. |
| Melt Mass-Flow Rate (MFR) | ASTM D1238 | 40 g/10 min |
| Mechanical |  |  |
| Tensile Strength @ Yield | ASTM D638 | 4060 psi |
| Tensile Elongation @ Yld | ASTM D638 | 12.00% |
| Flexural Modulus (Procedure A) | ASTM D790 | 1% Secant: 145000 psi |
| Impact |  |  |
| Notched Izod Impact (73° F.) | ASTM D256 | .0899 ft lb/in |

TABLE 1-continued

| | Test Method | Nominal Value Unit |
|---|---|---|
| Thermal | | |
| DTUL @66 psi— Unannealed | ASTM D648 | 194° F. |
| Optical Haze | ASTM D1003 | 6.00% |

In another embodiment, the injection molding material for the chassis components can be provided by DuraCetal™, also available from Myerson Tooth, Inc., which is a Poly-oxymethlene Copolymer with the following properties shown in Table 2:

TABLE 2

| | Test Method | Nominal Value Unit |
|---|---|---|
| Physical | | |
| Specific Gravity | ASTM D792 | 1.41 |
| Melt Mass-Flow Rate (MFR) | ASTM D1238 | |
| Mechanical | | |
| Tensile Strength | ASTM D638 | 8800 psi |
| Tensile Elongation | ASTM D638 | 60.00% |
| Flexural Modulus | ASTM D790 | .38 psi × 10$^6$ |
| Impact | | |
| Impact Strength, Izod, notched 1/8 in (3.18 mm) section | ASTM D256 | 1 ft-lb/in |
| Thermal | | |
| Deflection Temperature @ 264 psi (1.82 Mpa) | ASTM 648 | |
| Deflection Temperature @ 66 psi (0.45 Mpa) | ASTM D648 | 315 ƒC |

Referring now to FIG. 5, a flow diagram illustrates another embodiment is directed to a method for a dental appliance. In particular, block 510 provides for heating the dental appliance using elongated members to submerge dental appliance. For example, on dental appliance 100, without elastic straps 190, can be heated by boiling or other heat process so that reformable thermoplastic is heated to enable reformation. In one or more embodiments, the dental appliance includes an upper dental tray such as upper dental appliance chassis 120 and lower appliance chassis 110, each with a reformable thermoplastic layer.

Block 520 provides for molding the first reformable thermoplastic layer and the second reformable thermoplastic layer according to dentition of a patient. For example, first reformable thermoplastic layer, such as reformable thermoplastic layer 130 and reformable thermoplastic layer 140 can include a bond between hard lower and upper dental chassis coupled to reformable thermoplastic material. In some embodiments the bonding between the formable and reformable layers can be a combination of mechanical and chemical.

Block 530 provides for identifying a distance using marks on the elongated members for mandibular advancement. For example, marks 134 on elongated member 132 identify the distance, if any, from "21" 136 mark where the upper mark 114 on elongated member 112 comfortably advances a patient's mandible. This identifies the length of a band for coupling the upper and lower chassis of the dental appliance.

Block 540 provides for attaching at least two bands identified by the marks to couple the upper portion of the dental appliance to a lower portion of the dental appliance, wherein the upper portion includes the first reformable thermoplastic layer, and the lower portion of the dental appliance includes the second reformable thermoplastic layer, wherein the at least two bands attach a first pair of button protrusions with a second pair of button protrusions to provide a forward mandibular position when the two bands are attached to connect the upper dental tray and the lower dental tray.

Block 550 provides that if the dentition of the patient changes, the method provides for reheating the dental appliance to remold the first reformable thermoplastic layer and the second reformable thermoplastic layer.

In one or more embodiments, the heat process is a boil and bite heat process wherein a patient inserts a heated dental appliance to form the first and second reformable thermoplastic layers according to the dentition of the patient.

In one or more embodiments, the upper dental tray includes a first non-reformable layer coupled to the first reformable thermoplastic layer via injection overmolding and the lower dental tray includes a second non-reformable layer coupled to the second reformable thermoplastic layer via injection overmolding.

In one or more embodiments, the first reformable thermoplastic layer and second reformable thermoplastic layer are comprised of one or more of ε-caprolactone, caprolactam and one or more polycaprolactone polymers. For example, in some embodiments, the reformable thermoplastic layers can be formed of CAPA™ 6800 and/or CAPA™ 6500 thermoplastics.

In one or more embodiments, the lower dental tray includes a pair of vertical displacement bite pads. For example, the pair of vertical displacement bite pads could be part of the non-reformable chassis components. In one or more embodiments, the vertical displacement bite pads can be snap-on type bite pads. For example, the non-reformable chassis components can include a base enabling snap-on type bite pads to be switched out.

Figure 6:
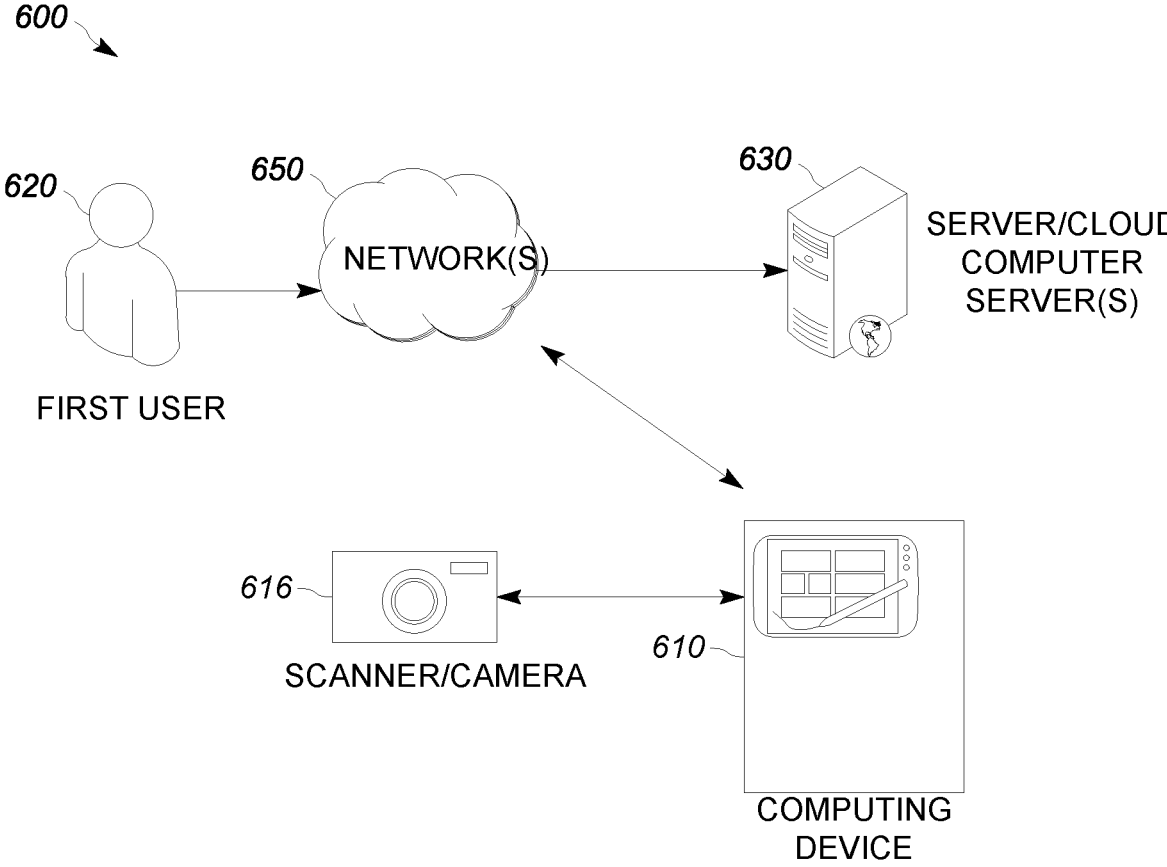
FIG. 6 illustrates a system and network environment including a computing device in accordance with one or more embodiments of the present disclosure.

Referring now to FIG. 6, the figure illustrates exemplary environment 600 including a computing device 610 connected to a scanner/camera 616, which in turn is connected to a first user 620 connected to a server/cloud computer servers 630 via network interface. As will be further described herein the illustrated computing device 610 and computer server 630 may employ the computationally implemented methods, systems, and articles of manufacture in accordance with various embodiments. The computing device 610 and computer server 630, in various embodiments, enable functions of the computing device 610.

Computing device 610 illustrated in FIG. 6 can be a tablet computer, in alternative embodiments, the computationally implemented methods, systems, and articles of manufacture in accordance with various embodiments may be embodied in other types of computer systems having other form factors including other types of portable computing devices such as, for example, mobile telephones, laptops, smartphones, e-readers, and so forth. Computing devices can include smartphones, client computers and the like as possible computing devices. As illustrated, the computing device 610 can include a display, such as a touchscreen as input/output of the computing device 610. Computing device 610 can further include a keyboard, either as a touch input/output keyboard or as an attached keyboard. As further depicted, the computing device 610 may also be connected to a scanner 616. In one embodiment, scanner 616 can be a scanning camera capable of creating a 3D image of dentition, and oral characteristics of a patient.

Figure 7:
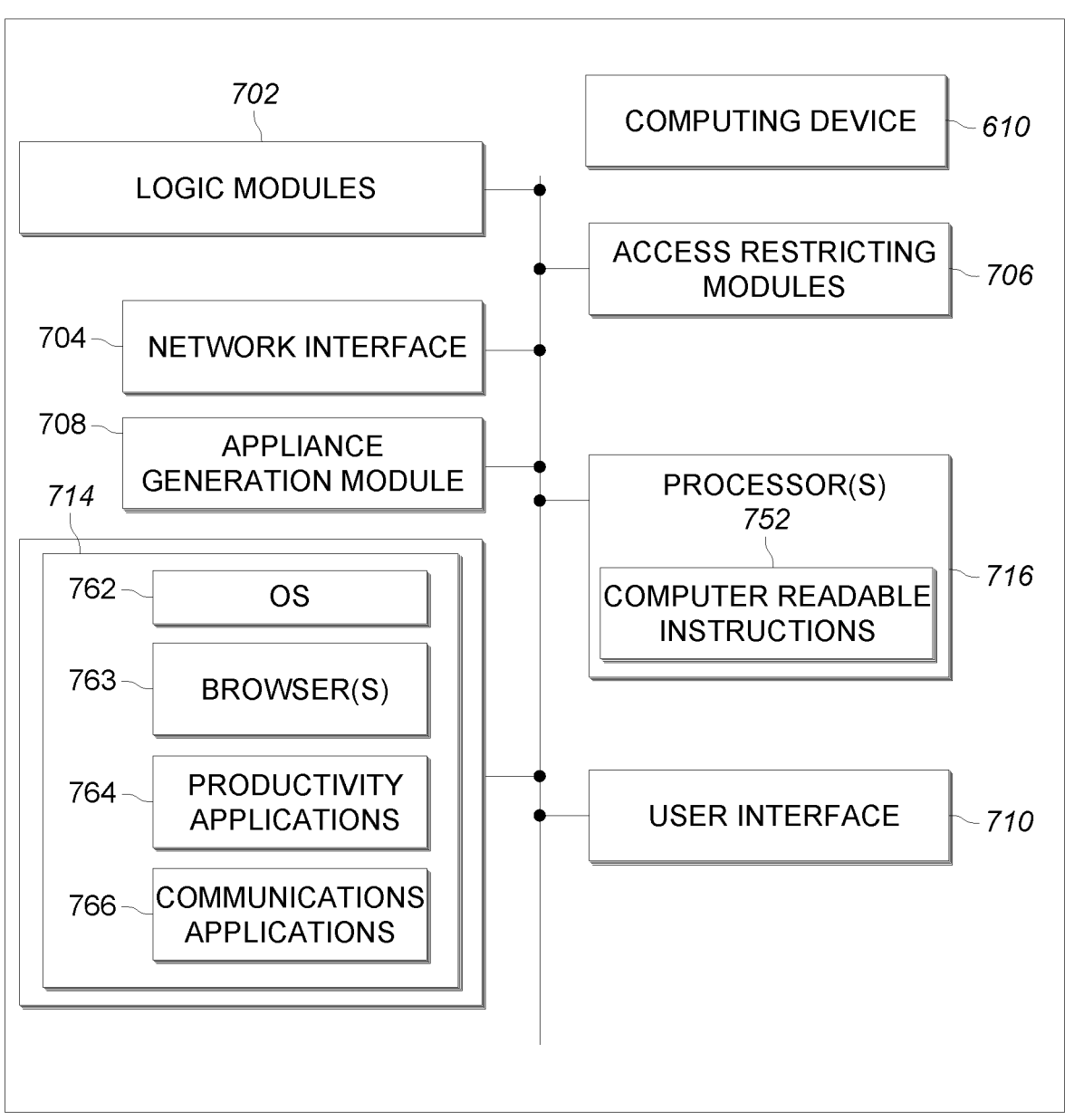
FIG. 7 illustrates a processor and a computing device in accordance with one or more embodiments of the present disclosure.

Referring now to FIG. 7, computing device 610 is further illustrated with logic modules 702, network interface 704, user interface 710, processor 716, which can include memory and computer readable instructions 752. Logic modules 702 can be implemented using circuit components such as an ASIC. Logic modules 702 and other modules shown, may be implemented using a combination of specifically designed circuitry such as ASIC and one or more processors 716 (or other types of circuitry such as field programmable gate arrays or FPGAs) executing computer readable instructions 752. For example, in some embodiments, at least one of the logic modules may be implemented using specially designed circuitry (e.g., ASIC) while a second logic module may be implemented using a processor 716 (or other types of programmable circuitry such as an FPGA) executing computer readable instructions 752 (e.g., software and/or firmware). System requirements could dictate a combination of software and firmware and circuitry to meet the embodiments herein, for example, logic modules could be designed to use the most efficient combination of software/hardware/firmware in order to quickly implement methods and systems within the scope of the present disclosure.

In various embodiments, the memory 714 of the computing device 610 may comprise of one or more of mass storage device, read-only memory (ROM), programmable read-only memory (PROM), erasable programmable read-only memory (EPROM), cache memory such as random access memory (RAM), flash memory, synchronous random access memory (SRAM), dynamic random access memory (DRAM), and/or other types of memory devices. In various embodiments, the one or more applications 764, 766 stored in memory may include, for example, an operating system 762, a browser(s) 763, and one or more productivity applications 764 such as a word processing application or an imaging application, scanning application and one or more communication applications 766.

Computing device 610 may also include access restricting module 706. Access restricting module 706 of the computing device 610 can be configured to restrict access via the computing device 610 or preventing one or more actions by computing device 610. Computing device 610 may also include appliance generation module 708 coupled to access restricting module 706 via a bus.

Figure 8:
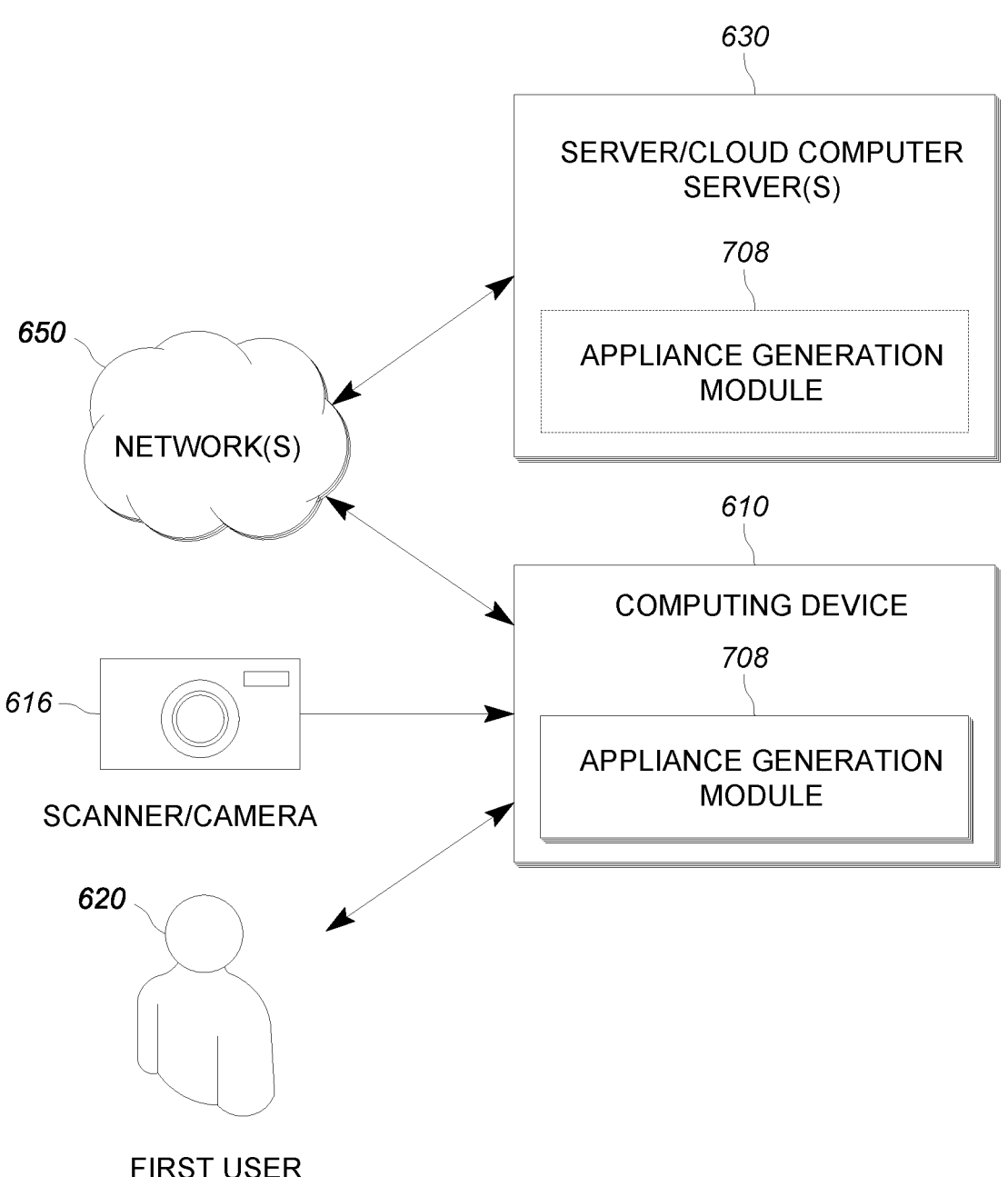
FIG. 8 illustrates a network environment in accordance with one or more embodiments of the present disclosure.

Referring to FIG. 8, appliance generation module 708 may be configured to determine that a first user 620 is an authorized user attempting to operate computing device 610. Appliance generation module 708 can also be configured to determine an established authorized user based on network received data while computing device 610 is connected to a network connection 650. In the case of appliance generation module 708, existing in a cloud computing setting or computer server 630, appliance generation module 708 may be configured to determine a network-based authorization for the first user when first logging into network 650 or cloud computing logging to computer server 630.

Appliance generation module 708 can be configured to receive inputs from a scanner 616.

Computer server 630 connecting via network 650 to the computing device 610 of FIGS. 6 and 7 can establish and/or determine a vertical displacement and a forward mandibular position for treating sleep apnea. For example, scanner 616 and/or molds of a patient's teeth can be examined and used to determine the adjustment needed for treating sleep apnea. Upper and lower chassis including button protrusions can be created from molds and injection molded prior to reformable thermoplastic layers are injection molded as an overmolding. For instance, a patient with malocclusion and sleep apnea will require a determination via scanner 616 or other method. Each patient, depending on the results of scanned teeth and soft tissue and patient feedback, may require a different placement of horizontal and vertical displacement for both treating sleep apnea. Vertical displacement can be by way of lower bite pads or by way of the thickness of a lower dental tray. In embodiments, the vertical displacement is part of the mold, milled appliance or 3D printed dental appliance.

In some embodiments, the elastic straps can be of different lengths and strengths to enable a gradual and incremental titration to advance the mandible forward, for example some are 21 mm long but may be softer or stronger elastic. In some embodiments, 9 different lengths may be offered and four different strengths may be offered for patient comfort and efficacy.

In one or more embodiments, bite pads 170 can be snap-on type bite pads according to a determined amount of vertical component required for a patient with sleep apnea, or height of bite pads for the dental appliance as a function of the shape of the soft palate. In other embodiments, the vertical displacement is determined by the soft tissue of the patient, such as the hyoid shape. In one or more embodiments, a scanner and/or camera such as scanner/camera 616 detects shape of soft palate. The data is collected as oral characteristic data and provided to a processor which operates to classify the oral characteristics for fabrication of the upper and lower dentition appliance chassis.

In one or more embodiments, there are three classifications for a soft palate: short, normal or long. Thus, in one or more embodiments, a method includes determining if the posterior edge of the soft palate is short. For example, if there is 5 to 7 mm of space between the posterior edge of the soft palate to the posterior wall of the oral pharynx, the soft palate is determined to be short, and a dental appliance will need 5 to 7 mm of vertical displacement. In some embodiments, to determine the vertical displacement, a scanner can measure the distance from the gingival-tooth crown juncture of the maxillary central to the gingival-tooth crown juncture of the mandibular central. If this distance is, for example, 20 mm and, thus, 7 mm of vertical is desired, in some embodiments, a vertical displacement can be determined such that the bite will have 7 mm of vertical displacement.

In some embodiments, a method includes determining if the posterior edge of the soft palate is longer than a normal soft palate. If the soft palate is longer such that the posterior edge of the soft palate has 3 to 4 mm of space between it and the posterior wall of the oral pharynx, in some embodiments, a dental appliance can be made to provide 8 to 10 mm of vertical displacement to keep the soft palate from closing the airway when the patient in a supine position.

If the soft palate is very long and webbed shaped with just 2 mm or less of space between the soft palate and the posterior wall of the oral pharynx, the appliance will likely require 11 to 14 mm of vertical. displacement.

In one or more embodiments, a scanner determines whether a soft palate is short, long or normal and determines the placement of the uvula with respect to the palate.

Determining the placement and size of the lower dental tray bite pads is a function of the length of the palate of a patient. Additionally, in some embodiments, maxillary button protrusions on an upper dental tray are placed on each incisal edge, in the embrasure between the right and left cuspids and first bicuspids.

The placement of the mandibular button protrusions (lower dental tray button protrustions) can be determined by determining a patient's range of motion. In some embodiments, a scanner detects maximal range of motion by measuring before and after extension of the lower jaw. For example, if the patient has only 5-7 mm of potential advancement, the buttons are placed 23 mm apart with the patient's teeth in centric. If the patient has 7-10 mm of potential advancement, the buttons are placed 25 mm apart, and if the patient has 10-17 mm of potential advancement, the buttons are placed 27 mm apart.

In one or more embodiments, a method includes determining the location of the buttons on the mandibular arch by occluding the patient's models in centric and placing the center of the mandibular button 23, 25, or 27 mm from the center of the maxillary button.

As described above, a scanner/camera 616 takes images/ scans of a patient's mouth to determine dentition data and/or soft palate data and a computer system coupled to the scanner or processor incorporated into a scanner/camera determines the placement of the button protrusions and bite pads on the upper and lower dental appliance chassis.

In one or more embodiments receiving oral characteristic data of the patient includes scanning by a scanner or camera a mold of the teeth; and transmitting the oral characteristic data to a server.

In one or more embodiments receiving oral characteristic data of a patient includes scanning by a scanner of an oral cavity of the patient; imaging the oral cavity to determine the dentition data, wherein the oral characteristic data includes dentition data as one or more images of teeth and a gum line of the patient and one or more images of a soft palate of the patient; and transmitting the oral characteristic to a server.

In one or more embodiments determining the oral characteristic data and vertical displacement is a function of a shape of the soft palate of the patient.

In one or more embodiments the determining via the oral characteristic the vertical displacement as a function of the shape of the soft palate of the patient includes determining a vertical displacement of between 5 and 7 millimeters if the soft palate has between 5 to 7 millimeters of space between a posterior edge of the soft palate to a posterior wall of an oral pharynx of the patient.

In one or more embodiments, the determining via the oral characteristic data the vertical displacement as a function of the shape of the soft palate of the patient includes processing the oral characteristic data to measure a distance from a gingival-tooth crown juncture of a maxillary central to a gingival-tooth crown juncture of a mandibular central.

In one or more embodiments the determining via the oral characteristic data the vertical displacement as a function of the shape of the soft palate of the patient includes determining if a posterior edge of the soft palate is longer than a normal soft palate with between 3 and 5 millimeters of space between a posterior edge of the soft palate to a posterior wall of an oral pharynx of the patient; and providing the vertical displacement of between 8 and 10 millimeters.

In one or more embodiments the determining via the oral characteristic data the vertical displacement as a function of the shape of the soft palate of the patient includes determining if a posterior edge of the soft palate is longer than a normal soft palate and webbed and wherein two millimeters or less of space exists between the soft palate and a posterior wall of an oral pharynx, providing at least 11 to 14 millimeters for the vertical displacement.

In one or more embodiments the determining via the oral characteristic data the vertical displacement as a function of the shape of the soft palate of the patient includes determining whether the soft palate is one of short, normal, and long.

In one or more embodiments the lower dental tray is inclusive of a first vertical displacement bite pad on a left side of the lower dental tray and a second vertical displacement bite pad on a right side of the lower dental tray wherein a height of each of the first and second vertical displacement bite pads is determined according to the oral characteristic data, the oral characteristic data providing soft tissue data of the patient indicative of airway function.

In one or more embodiments, the lower dental tray couples to the upper dental tray via two elastic bands coupled to either side of the dental appliance via the button protrusions. The elastic bands can include a plurality of pairs of elastic bands, each pair being of different length and/or elasticity.

Some embodiments of a method may include, a method including forming an upper dental appliance chassis including at least two upper appliance button protrusions; forming a lower dental appliance chassis including at least two lower appliance button protrusions and at least two vertical displacement bite pads; injection overmolding a first thermoplastic on the upper dental appliance chassis to provide a first reformable thermoplastic layer integrated with the upper dental appliance chassis that exposes the at least two upper appliance button protrusions to form an upper dental tray; and injection overmolding a second thermoplastic on the upper dental appliance chassis to provide a second reformable thermoplastic layer integrated with the lower dental appliance chassis that exposes the at least two lower appliance button protrusions and the at least two vertical displacement bite pads to form a bottom dental tray.

In one or more embodiments, the method includes forming a dental appliance including the lower dental tray and an upper dental tray, each of the lower dental tray and the upper dental tray, the lower dental tray inclusive of the at least two vertical displacement bite pads and at least two lower appliance button protrusions, the upper dental tray inclusive of the at least two upper appliance button protrusions, the at least two lower appliance button protrusions and the at least two upper appliance button protrusions providing a forward mandibular position when two elastic bands are attached to connect the upper dental tray and the lower dental tray.

In one or more embodiments, the upper dental appliance chassis and the lower dental appliance chassis are injection molded from one or more of an Ethylene Propylene Copolymer and a Polyoxymethlene Copolymer.

In one or more embodiments, the upper dental appliance chassis and the lower dental appliance chassis are injection molded using a thermoplastic olefin, thermoplastic polyolefin, or olefinic thermoplastic elastomer.

In one or more embodiments, the upper dental appliance chassis and the lower dental appliance chassis are injection molded using a polyethylene terephthalate.

In one or more embodiments, the upper dental appliance chassis and the lower dental appliance chassis are formed by three-dimensional (3D) printing of one or more of a light polymerizable liquid thermoset crosslinked polymer, a polyurethane, a methacrylate and a copolymer.

In one or more embodiments, the upper dental appliance chassis and the lower dental appliance chassis are formed by three-dimensional (3D) printing of a polymerizable resin composition of a urethane monomer of urethane dimethacrylate (UDMA), an acidic monomer, and one or more hydrophobic monomers.

In one or more embodiments, the first thermoplastic and the second thermoplastic are comprised of one or more of an ε-caprolactone, caprolactam and one or more polycaprolactone polymers.

In one or more embodiments, the first thermoplastic and the second thermoplastic are comprised of one or more of a caprolactone or polycaprolactone polymer material overmolded on the upper dental appliance chassis and the lower dental appliance chassis.

In one or more embodiments, the first thermoplastic and the second thermoplastic provide bonded overshot dentition layers that are formable to a patient's dentition via a heat process.

In one or more embodiments, the first thermoplastic and the second thermoplastic provide bonded overshot dentition layers that are reformable to altered dentition of the patient via one or more subsequent heat processes.

In one or more embodiments, the heat process includes a boil and bite process.

In one or more embodiments, the at least two vertical displacement bite pads are configured to be replaced with alternate vertical displacement bite pads of one or more heights.

Another embodiment is directed to a system comprising a processor and a non-transitory computer-readable storage medium storing instructions operative when executed on the processor to form a dental appliance including forming an upper dental appliance chassis including at least two upper appliance button protrusions; forming a lower dental appliance chassis including at least two lower appliance button protrusions and at least two vertical displacement bite pads; injection overmolding a first thermoplastic on the upper dental appliance chassis to provide a first reformable thermoplastic layer integrated with the upper dental appliance chassis that exposes the at least two upper appliance button protrusions to form an upper dental tray; and injection overmolding a second thermoplastic on the upper dental appliance chassis to provide a second reformable thermoplastic layer integrated with the lower dental appliance chassis that exposes the at least two lower appliance button protrusions and the at least two vertical displacement bite pads to form a bottom dental tray.

Another embodiment is directed to a method including heating a dental appliance by a heat process, the dental appliance including an upper dental tray with a first reformable thermoplastic layer and a lower dental tray with a second reformable thermoplastic layer; molding the first reformable thermoplastic layer and the second reformable thermoplastic layer according to dentition of a patient; and attaching at least two elastic straps to the dental appliance to couple an upper portion of the dental appliance to a lower portion of the dental appliance, wherein the upper portion includes the first reformable thermoplastic layer, and the lower portion of the dental appliance includes the second reformable thermoplastic layer, the at least two elastic straps, the at least two elastic straps attaching a first pair of button protrusions with a second pair of button protrusions to provide a forward mandibular position when the two elastic bands are attached to connect the upper dental tray and the lower dental tray.

One or more embodiments further include, if the dentition of the patient changes, reheating the dental appliance to remold the first reformable thermoplastic layer and the second reformable thermoplastic layer.

In one or more embodiments, the heat process is a boil and bite heat process wherein a patient inserts a heated dental appliance into form the first and second reformable thermoplastic layers according to the dentition of the patient.

In one or more embodiments, the upper dental tray includes a first non-reformable layer coupled to the first reformable thermoplastic layer via injection overmolding and the lower dental tray includes a second non-reformable layer coupled to the second reformable thermoplastic layer via injection overmolding.

In one or more embodiments, the first reformable thermoplastic layer and second reformable thermoplastic layer are comprised of one or more of $\varepsilon$-caprolactone, caprolactam and one or more polycaprolactone polymers.

In one or more embodiments, the lower dental tray includes a pair of vertical displacement bite pads with a gradient from rear to fore of at least 1 millimeter.

Another embodiment is directed to a mandibular advancement dental appliance including a two-layer lower tray including: a lower dental appliance chassis layer including at least two lower appliance button protrusions and at least two vertical displacement bite pads; and a first reformable thermoplastic layer injection overmolded over the lower dental appliance chassis layer formed of one or more of an $\varepsilon$-caprolactone, caprolactam and one or more polycaprolactone polymers integrated with the lower dental appliance chassis via one or more cavities in the surface of the lower dental appliance chassis, the first reformable thermoplastic layer configured to expose the at least two lower appliance button protrusions and the at least two vertical displacement bite pads; and a two-layer upper tray including: an upper dental appliance chassis layer including at least two upper appliance button protrusions; and a second reformable thermoplastic layer injection overmolded over the upper dental appliance chassis layer formed of one or more of an $\varepsilon$-caprolactone, caprolactam and one or more polycaprolactone polymers integrated with the upper dental appliance chassis via one or more cavities in the surface of the upper dental appliance chassis, the first reformable thermoplastic layer configured to expose the at least two lower appliance button protrusions.

In one or more embodiments, the mandibular advancement dental appliance includes a pair of elastic straps adapted to couple the two-layer lower tray with the two-layer upper tray to provide mandibular advancement.

Some embodiments include a processor and a non-transitory computer-readable storage medium storing instructions operative when executed on the processor to perform the methods herein described.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware in one or more machines or articles of manufacture), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation that is implemented in one or more machines or articles of manufacture; or, yet again alternatively, the implementer may opt for some combination of hardware, software, and/or firmware in one or more machines or articles of manufacture. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware in one or more machines or articles of manufacture.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuitry (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuitry, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

What is claimed:

1. A method comprising:
    forming an upper dental appliance chassis including at least two upper appliance button protrusions and an elongated member protruding from the upper dental appliance chassis;
    forming a lower dental appliance chassis including at least two lower appliance button protrusions, at least two vertical displacement bite pads, and a second elongated member protruding from the lower dental appliance chassis;
    injection overmolding a first thermoplastic on the upper dental appliance chassis to provide a first reformable layer integrated with the upper dental appliance chassis that exposes the at least two upper appliance button protrusions to form an upper dental tray; and
    injection overmolding a second thermoplastic on the lower dental appliance chassis to provide a second reformable layer integrated with the lower dental appliance chassis that exposes the at least two lower appliance button protrusions and the at least two vertical displacement bite pads to form a bottom dental tray, wherein the at least two vertical displacement bite pads include a gradient inclining from rear to fore.

2. The method of claim 1 further comprising:
    forming a dental appliance including the upper dental appliance chassis and the lower dental appliance chassis, wherein the at least two lower appliance button protrusions, and the at least two upper appliance button protrusions provide a forward mandibular position when two or more bands are attached to connect the upper dental tray and the lower dental tray.

3. The method of claim 1 wherein the upper dental appliance chassis and the lower dental appliance chassis are injection molded from one or more of an ethylene propylene copolymer and a polyoxymethylene copolymer.

4. The method of claim 1 wherein the upper dental appliance chassis and the lower dental appliance chassis are injection molded using at least one of a thermoplastic olefin, a thermoplastic polyolefine, and an olefinic thermoplastic elastomer.

5. The method of claim 1 wherein the upper dental appliance chassis and the lower dental appliance chassis are injection molded using a polyethylene terephthalate.

6. The method of claim 1 wherein the upper dental appliance chassis and the lower dental appliance chassis are formed by three-dimensional (3D) printing of one or more of a light polymerizable liquid thermoset crosslinked polymer, a polyurethane, a methacrylate and a copolymer.

7. The method of claim 1 wherein the upper dental appliance chassis and the lower dental appliance chassis are formed by three-dimensional (3D) printing of a polymerizable resin composition of a urethane monomer of urethane dimethacrylate (UDMA), an acidic monomer, and one or more hydrophobic monomers.

8. The method of claim 1 wherein the first thermoplastic and the second thermoplastic are comprised of one or more of an ε-caprolactone, caprolactam and one or more polycaprolactone polymers.

9. The method of claim 1 wherein the first thermoplastic and the second thermoplastic are comprised of one or more of a caprolactone and a polycaprolactone polymer material overmolded on the upper dental appliance chassis and the lower dental appliance chassis.

10. The method of claim 1 wherein the at least two vertical displacement bite pads are configured to be replaced with alternate vertical displacement bite pads of one or more heights.

11. A mandibular advancement dental appliance comprising:
a two-layer upper tray including:
an upper dental appliance chassis layer including at least two upper appliance button protrusions and a first elongated member protruding from the upper dental appliance chassis; and a first reformable thermoplastic layer injection over-molded over a portion of the upper dental appliance chassis layer formed of one or more of an ε-caprolactone, caprolactam and one or more polycaprolactone polymers integrated with the upper dental appliance chassis via one or more cavities in the surface of the upper dental appliance chassis, the first reformable thermoplastic layer configured to expose the at least two upper appliance button protrusions; and
a two-layer lower tray including:
a lower dental appliance chassis layer including at least two lower appliance button protrusions and at least two vertical displacement bite pads, and a second elongated member protruding from the lower dental appliance chassis; and
a second reformable thermoplastic layer injection over-molded over the lower dental appliance chassis layer formed of one or more of an ε-caprolactone, caprolactam and one or more polycaprolactone polymers integrated with the lower dental appliance chassis via one or more cavities in the surface of the lower dental appliance chassis, the second reformable thermoplastic layer configured to expose the at least two lower appliance button protrusions and the at least two vertical displacement bite pads.

12. The mandibular advancement dental appliance of claim 11, further comprising:
a pair of bands adapted to couple the two-layer lower tray with the two-layer upper tray to provide mandibular advancement.

13. The mandibular advancement dental appliance of claim 11, wherein the first elongated member and the second elongated member include marks to measure forward mandibular adjustment when worn by a patient.

14. The mandibular advancement dental appliance of claim 11, wherein at least one of the first elongated member and the second elongated member includes a default 21 millimeter marking, and at least one of the first elongated member and second elongated member includes marks that identify a displacement matching a length for the pair of bands.

15. The mandibular advancement dental appliance of claim 11, wherein the at least two vertical displacement bite pads are formed with a gradient inclining from rear to fore.

* * * * *